United States Patent [19]

Jaunin et al.

[11] Patent Number: 4,994,612
[45] Date of Patent: Feb. 19, 1991

[54] YLIDENE SULFONAMIDE DERIVATIVES

[75] Inventors: Roland Jaunin, Basle; Henri Ramuz, Birsfelden, both of Switzerland

[73] Assignee: Hoffmann-La Roche Inc., Nutley, N.J.

[21] Appl. No.: 336,176

[22] Filed: Apr. 11, 1989

Related U.S. Application Data

[62] Division of Ser. No. 871,026, Jun. 5, 1986, Pat. No. 4,847,273.

[30] Foreign Application Priority Data

Jun. 21, 1985 [CH] Switzerland .......................... 2651/85

[51] Int. Cl.$^5$ .......................................... C07C 311/12
[52] U.S. Cl. ..................................... 564/88; 546/216;
546/331; 548/952; 548/965; 548/542; 548/341; 548/343; 540/604; 540/482; 544/158
[58] Field of Search ................. 564/88; 546/216, 331; 548/952, 965, 542, 341, 343; 540/604, 482; 544/158

[56] References Cited

FOREIGN PATENT DOCUMENTS 3323511 1/1985 Fed. Rep. of Germany .

Primary Examiner—Jane T. Fan
Attorney, Agent, or Firm—George M. Gould; Bernard S. Leon; William G. Isgro

[57] ABSTRACT

Dihydropyridine derivatives of the formula

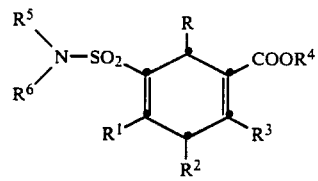

wherein the symbols R and $R^1$ to $R^6$ have the significance given in claim 1, have a pronounced calcium-antagonist activity and can accordingly be used as medicaments, especially in the control or prevention of angina pectoris, ischemia, high blood pressure and/or migraine. The compounds of formula I can be prepared by reacting an ylidene compound of the formula

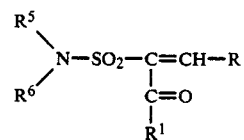

with an enamine of the formula

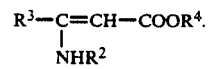

6 Claims, No Drawings

YLIDENE SULFONAMIDE DERIVATIVES

This is a division of application Ser. No. 06/871,026 filed June 5, 1986 now U.S. Pat. No. 4,847,273, granted July 11, 1989.

The invention relates to dihydropyridine derivatives. In particular, it relates to dihydropyridine derivatives of the formula

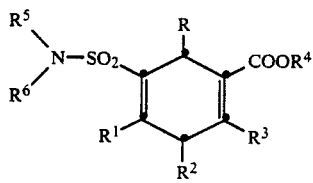

wherein R is aryl or a heterocyclic residue with up to three hetero atoms selected from oxygen, nitrogen and sulfur, $R^1$ and $R^3$ each independently, is $C_1$–$C_4$-alkyl or $C_3$–$C_6$-cycloalkyl, $R^2$ is hydrogen or $C_1$–$C_4$-alkyl, $R^4$ is $C_1$–$C_6$-alkyl, $C_3$–$C_6$-alkenyl, $C_3$–$C_6$-alkynyl, $C_3$–$C_6$-cycloalkyl, $C_3$–$C_6$-cycloalkyl-$C_1$–$C_6$-alkyl, cyano-$C_2$–$C_6$-alkyl, halo-$C_2$–$C_6$-alkyl, hydroxy-$C_2$–$C_6$-alkyl, $\omega,\omega,\omega$-trifluoro-$C_1$–$C_6$-alkyl, $C_1$–$C_6$-alkoxy-$C_1$–$C_6$-alkyl, $C_1$–$C_6$-alkoxy-$C_1$–$C_6$-alkoxy-$C_1$–$C_6$-alkyl, $C_1$–$C_6$-alkoxycarbonyl-$C_2$–$C_6$-alkyl, $C_1$–$C_4$-alkanoyloxy-$C_1$–$C_6$-alkyl, $C_3$–$C_6$-alkenyloxy-$C_1$–$C_6$-alkyl, $C_1$–$C_6$-alkylthio-$C_1$–$C_6$-alkyl, benzyloxy-$C_1$–$C_6$-alkyl, phenyl optionally substituted by halogen, cyano, di-$C_1$–$C_6$-alkyl-amino, $C_1$–$C_6$-alkoxy, $C_1$–$C_6$-alkyl, trifluoromethyl or nitro or phenyl-$C_1$–$C_6$-alkyl optionally substituted by halogen, cyano, di-$C_1$–$C_6$-alkyl-amino, $C_1$–$C_6$-alkoxy, $C_1$–$C_6$-alkyl, trifluoromethyl or nitro, $R^5$ is hydrogen, $C_1$–$C_6$-alkyl or $C_3$–$C_6$-cycloalkyl, $R^6$ is $C_1$–$C_6$-alkyl, $C_3$–$C_6$-cycloalkyl, $C_3$–$C_6$-cycloalkyl-$C_1$–$C_6$-alkyl, $C_1$–$C_6$-alkoxy-$C_1C_6$-alkyl, $C_1$–$C_6$-alkoxy-$C_1$–$C_6$-alkyl, $C_1$–$C_6$-alkylthio-$C_1$–$C_6$-alkyl, $C_1$–$C_6$-alkoxycarbonyl-$C_2$–$C_6$-alkyl or $R^5$ and $R^6$ taken together are the group -$CH_2CH_2$-O-$CH_2CH_2$-or or a -$(CH_2)_n$- group in which n is an integer of 2 to 7, in the form of stereoisomers, diastereoisomeric mixtures racemates and optical antipodes.

The compounds of formula I are useful in the control or prevention of illnesses or in the improvement of health, especially in the control or prevention of angina pectoris, ischemia, high blood pressure and migraine.

DETAILED DESCRIPTION OF THE INVENTION

The invention relates to dihydropyridine derivatives. In particular, it relates to dihydropyridine derivatives of the formula

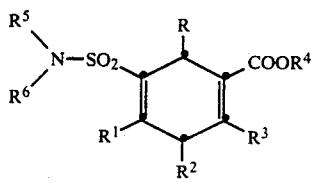

wherein R is aryl or a heterocyclic residue with up to three hetero atoms selected from oxygen, nitrogen and sulfur, $R^1$ and $R^3$ each independently, is $C_1$–$C_4$-alkyl or $C_3$–$C_6$-cycloalkyl, $R^2$ is hydrogen or $C_1$–$C_4$-alkyl, $R^4$ is $C_1$–$C_6$-alkyl, $C_3$–$C_6$-alkenyl, $C_3$–$C_6$-alkynyl, $C_3$–$C_6$-cycloalkyl, $C_3$–$C_6$-cycloalkyl-$C_1$–$C_6$-alkyl, cyano-$C_2$–$C_6$-alkyl, halo-$C_2$–$C_6$-alkyl, hydroxy -$C_2$–$C_6$-alkyl, $\omega,\omega,\omega$-trifluoro-$C_1$–$C_6$-alkyl, $C_1$–$C_6$-alkoxy-$C_1$–$C_6$-alkyl, $C_1$–$C_6$-alkoxy-$C_1$–$C_6$-alkyl, $C_1$–$C_6$-alkoxy-$C_1$–$C_6$-alkoxy-$C_1$–$C_6$-alkyl, $C_1$–$C_4$-alkanoyloxy-$C_1$–$C_6$-alkyl, $C_3$–$C_6$-alkenyloxy-$C_1$–$C_6$-alkyl, $C_1$–$C_6$-alkylthio-$C_1$–$C_6$-alkyl, benzyloxy-$C_1$–$C_6$-alkyl, phenyl optionally substituted by halogen, cyano, di-$C_1$–$C_6$-alkyl-amino, $C_1$–$C_6$-alkoxy, $C_1$–$C_6$-alkyl, trifluoromethyl or nitro or phenyl-$C_1$–$C_6$-alkyl optionally substituted by halogen, cyano, di-$C_1$–$C_6$-alkylamino, $C_1$–$C_6$-alkoxy, $C_1$–$C_6$-alkyl. trifluoromethyl or nitro, $R^5$ is hydrogen, $C_1$–$C_6$-alkyl or $C_3$–$C_6$-cycloalkyl, $R^6$ is $C_1$–$C_6$-alkyl, $C_3$–$C_6$-cycloalkyl, $C_3$–$C_6$-cycloalkyl-$C_1$–$C_6$-alkyl, $C_1$–$C_6$-alkoxy-$C_1$–$C_6$-alkyl, $C_1$–$C_6$-alkoxy-$C_1$–$C_6$-alkoxy-$C_1$–$C_6$-alkoxy-$C_1$–$C_6$-alkyl, $C_1$–$C_6$-alkylthio-$C_1$–$C_6$-alkyl, $C_1$–$C_6$alkoxycarbonyl-$C_2$–$C_6$-alkyl or $R^5$and $R^6$ taken together are the group —$CH_2CH_2$—O—$CH_2CH_2$— or a —$(CH_2)_n$—group in which n is an integer of 2 to 7, in the form of stereoisomers. diastereoisomeric mixtures. racemates and optical antipodes.

The compounds of formula I are distinguished by valuable pharmacodynamic properties.

Objects of the present invention comprise compounds of formula I per se and for use as therapeutically active substances, the preparation of these compounds, intermediates for the preparation of these compounds, medicaments containing these compounds and the p reparation of such medicaments, as well as the use of compounds of formula I in the control or prevention of illnesses or in the improvement of health, especially in the control or prevention of angina pectoris, ischemia, high blood pressure and migraine.

The term "alkyl" as used in the present description alone—or in combination—denotes straight-chain and branched, saturated hydrocarbon residues with the number of carbon atoms given in the respective case, such as, methyl, ethyl, n-propyl, isopropyl, n-butyl, isobutyl, sec.-butyl. tert.-butyl and the like. The term "alkoxy" denotes alkyl ether groups in which the term "alkyl" has the above significance. The term "$C_3$–$C_6$-alkenyl" denotes straight-chain and branched hydrocarbon groups with 3–6 carbon atoms in which at least one carbon-carbon bond is unsaturated such as allyl, butenyl and the like. The term "$C_3$–$C_6$-alkenyloxy" denotes alkenyl ether groups in which the term "$C_3$–$C_6$-alkenyl" is as described above. The term "$C_3$–$C_6$-alkynyl" denotes straight-chain and branched hydrocarbon groups with 3–6 carbon atoms in which at least one carbon-carbon triple bond is present such as propargyl and the like. The term "$C_3$–$C_6$-cycloalkyl" denotes cyclic, saturated hydrocarbon residues with 3–6 carbon atoms, such as cyclopropyl. cyclohexyl and the like. The term "$C_1$–$C_4$-alkanoyloxy" denotes the acyloxy residue of an alkanecarboxylic acid with 1–4 carbon atoms, such as, formyloxy, acetoxy, propionyloxy, butyryloxy and the like. The term "halogen" denotes the four halogen atom fluorine, chlorine, bromine and iodine. The term "aryl" denotes a mono- or bicyclic aromatic hydrocarbon residue with up to 10 carbon atoms in the aromatic ring structure which is optionally mono-, di- or tri-substituted by phenyl, $C_1$–$C_6$-alkyl, $C_3$–$C_6$- alkenyl, $C_3$–$C_6$-alkynyl, $C_1$–$C_6$-alkoxy, halogen, trifluoromethyl, trifluoromethoxy, difluoromethoxy, trifluoromethylthio, difluoromethylthio, nitro, cyano, axido, $C_1$–$C_6$-alkoxycarbonyl, aminocarbonyl, aminosulfonyl, $C_1$–$C_6$-alkylthio, $C_1$–$C_6$-alkylsulfonyl or $C_1$–$C_6$-alkanoyl or which is optionally disubstituted by $C_3$–$C_5$-alkylene or dioxy-$c_1$–$C_2$-alkylene, such as, chlorophenyl, tolyl, α, α, α-trifluorotolyl, dischlorophenyl, chloronitrophenyl, naphthyl and the like. The term "heterocyclic residue" embraces 5- and 6-membered mono- and bicyclic, heterocycles which are optionally mono-, di- or tri-substituted by phenyl, $C_1$–$C_6$-alkyl, $C_3$–$C_6$-alkenyl, $C_3$–$C_6$-alkynyl, $C_1$–$C_6$-alkoxy, halogen, trifluoromethyl, trifluoromethoxy, difluoromethoxy, trifluoromethylthio, difluoromethylthio, nitro, cyano, azido, $C_1$–$C_6$-alkoxycarbonyl, aminocarbonyl, aminosulfonyl, $C_1$–$C_6$-alkylthio, $C_1$–$C_6$-alkylsulfonyl or $C_1$–$C_6$-alkanoyl or which are optionally disubstituted $C_3$–$C_5$-alkylene or dioxy-$C_1$–$C_2$-alkylene, such as, thienyl, furyl, pyrryl, pyrazolyl, imidazolyl, oxazolyl, isoxazolyl, thiazolyl, isothiazolyl, pyridyl, N-oxidopyridyl, pyridazinyl, pyrimidyl, pyrazinyl, quinolyl, isoquinolyl, indolyl, benzimidazolyl, quinazolyl, quinoxalyl, (2,1,3-benzoxadiazol)-4-yl, (2,1,3-benzothiadiazol)-4-yl benzofuranyl, benzothienyl, benzoxazolyl, benzisoxazolyl, benzothiazolyl, benzisothiazolyl, indazolyl and the like. The term "$C_1$–$C_6$-alkanoyl" denotes the acyl residue of an alkanecarboxylic acid with 1–6 carbon atoms, such as, formyl, acetyl, propionyl, butyryl and the like.

A preferred class of compounds of formula I comprises those in which $R^4$ is $C_1$–$C_6$-alkyl, cyano-$C_2$–$C_6$-alkyl, halo-$C_2$–$C_6$-alkyl, hydroxy-$C_2$–$C_6$-alkyl, ω,ω,ω-trifluoro-$C_1$–$C_4$-alkanoyloxy-$C_1$–$C_6$-alkoxy-$C_1$–$C_6$-alkyl, $C_1$–$C_4$-alkanoyloxy-$C_1$–$C_6$-alkyl, benzylox-$C_1$–$D_6$-alkyl or phenyl-$C_1$–$C_6$-alkyl optionally substituted by halogen $R^6$ is $C_1$–$C_6$-alkyl, $R^6$ is $C_1$–$C_6$-alkyl, $C_1$–$C_6$-alkoxy-$C_1$–$C_6$-alkyl or $C_1$–$C_6$-alkoxycarbonyl-$C_2$–$C_6$-alkyl or $R^5$ and $R^6$ taken together are a -$(CH_2)_n$-group in which n is an integer of 2 to 7 and R is naphthyl, phenyl optionally monosubstituted by $C_1$–$C_6$-alkyl, halogen, trifluoromethyl or nitro or optionally disubstituted by halogen or halogen and nitro imidazolyl or pyridyl.

A more preferred class of compounds of formula I comprises those in which R is aryl, preferably phenyl substituted by $C_1$–$C_6$-alkyl halogen trifluoromethyl or nitro and especially 3-nitro-phenyl, 2-chloro-5-nitrophenyl or 2,5-dichlorophenyl, $R^1$ preferably is methyl. The preferred significance of $R^2$ is hydrogen. $R^3$ preferably is $C_1$–$C_4$-alkyl, especially methyl. Further, still more preferred compounds of formula I are those in which $R^4$ is $C_1$–$C_6$-alkyl, cyano-$C_2$–$C_6$-alkyl, halo-$C_2$–$C_6$-alkyl, hydroxy-$C_2$–$C_6$-alkyl, ω,ω,ω-trifluoro-$C_1$–$C_6$-alkyl, $C_1$–$C_6$-alkoxy-$C_1$–$C_6$-alkyl, $C_1$–$C_4$-alkanoyloxy-$C_1$–$C_6$-alkyl, benzyloxy-$C_1$–$C_6$-alkyl or phenyl-$C_1$–$C_6$-alkyl optionally substituted by halogen preferable $C_1$–$C_6$-alky, ω,ω,ω-trifluoro-$C_1$–$C_6$-alkyl, $C_1$–$C_6$-alkyl, $C_1$–$C_6$-alkoxy-$C_1$–$C_6$-alkyl or phenyl-$C_1$–$C_6$-alkyl, especially methyl, isopropyl, 2,2,2-trifluoroethyl, 2-propoxyethyl or 1-phenylethyl. $R^5$ preferably is $C_1$–$C_6$-alkyl, especially methyl, ethyl or isopropyl. The preferred significance of $R^6$ is $C_1$–$C_6$-alkyl or $C_1$–$C_6$-alkoxy-$C_1$–$C_6$-alkyl, especially methyl, ethyl, isopropyl, butyl or methoxyethyl.

From the above it follows that there are particularly preferred those compounds of formula I in which R signifies 3-nitrophenyl. 2-chloro-5-nitrophenyl or 2,5-dichlorophenyl, $R^1$ and $R^3$ each is methyl, $R^2$ is hydrogen, $R^4$ is methyl, isopropyl, 2,2,2-trifluoroethyl 2-propoxyethyl or 1-phenylethyl, $R^5$ is methyl, ethyl or isopropyl and $R^6$ is methyl, ethyl, isopropyl, butyl or methoxyethyl.

The most preferred group of compounds of formula I comprises those in which R is 3-nitrophenyl, $R^1$ and $R^3$ each is methyl, $R^2$ is hydrogen, $R^4$ is isopropyl or 2-propoxyethyl, $R^5$ $pl$ is methyl and $R^6$ is methyl butyl or methoxyethyl.

The most preferred compounds of formula I are:
5-(Dimethylylsulfamoyl)-1,4-dihydro-2,6-dimethyl-4-(3- -nitrophenyl)nicotinic acid 2-propoxyethyl ester.
5-(butylmethylsulfamoyl)-1,4-dihydro-2,6-dimethyl-4-(3-nitrophenyl) nicotinic acid isopropyl ester and
1,4-dihydro-2,6-dimethyl-5-[(2-methoxyethyl)methylsulfamoyl]-4-(3-nitrophenyl)nicotinic acid isopropyl ester.

The compounds of formula I can be prepared in accordance with the invention by reacting an ylidene compound of the formula

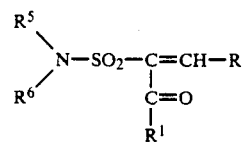

II wherein R, $R^1$, $R^5$ and $R^6$ are as previously described, with an enamine of the formula

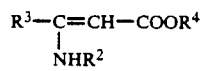

III wherein $R^2$, $R^3$ and $R^4$ are as previously described, and if desired, separating a stereoisomeric mixture obtained into its stereoisomers.

The reaction of an ylidene compound of formula II with an enamine of formula III is carried out according to known methods in the presence of an acid such as p-toluenesulfonic acid or DL-camphor-10-sulfonic acid or the H+form of a cation exchanger such as for example, Amberlyst ®15 in an inert solvent or solvent mixture at a temperature between about 20° and 150° C., preferably at the reflux temperature of the solvent or solvent mixture. Suitable solvents for this purpose are, for example, alcohols such as methanol, ethanol or isopropanol, ethers such as diethyl ether, dioxane, tetrahydrofuran glycol monomethyl ether or glycol dimethyl ether dimethylformamide, dimethyl sulfoxide or acetonitrile. Although the pressure is not critical and the reaction can be carried out readily at elevated pressure, for reasons of convenience the reaction is preferably carried out at normal atmospheric pressure. The two starting materials are preferably used in equimolar amounts.

The ylidene compounds of formula II form part of the invention. They can be prepared from ketosulfonamides of the formula

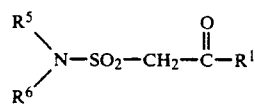

IV wherein $R^1$,$R^5$ and $R^6$ are as previously described. by reaction with an aldehyde of the formula

 V wherein R is as previously described. The reaction is carried out according to known methods under water-cleaving conditions, for example by heating to reflux in an inert organic solvent such as an aromatic hydrocarbon, for example, benzene or toluene, and the azeotropic removal of the water which is formed. The ketosulfonamides of formula IV are known or can be prepared in an analogous manner to that described in the literature.

The aldehydes of formula V above are known or can be obtained in an analogous manner to the preparation of the known compounds.

The compounds of formula I contain at least one asymmetric center (4-position) and can therefore exist as optical antipodes or as racemates. Compounds of formula I which contain more than one asymmetric center can exist in various diastereoisomeric forms. The present invention embraces all possible stereoisomers of compounds of formula I and all possible diastereoisomeric mixtures and racemates, as well as the separation of these diastereoisomeric mixtures which can be carried out according to known methods.

The compounds of formula I have a pronounced therapeutic calcium-antagonist activity and can accordingly be used as medicaments, especially for the control or prevention of angina pectoris, ischemia high blood pressure and migraine.

The calcium-antagonist activity as well as the blood pressure-lowering properties of the compounds in accordance with the invention can be demonstrated in the tests described hereinafter A. $^3$H-Nifedipine binding determination The determination is carried out on homogenates or on partially-cleaned membranes of rabbit or guinea pig heart. The reaction mixture (0.3 ml) consists of 0.2–0.8 mg of membrane protein, 1 nm of $^3$H-nifedipine (or 0.25 nM of $^3$H-nitrendipine) and various concentrations of the test substance. The incubation lasts 30 minutes at 25° C. or 37° C. and is stopped by dilution with the incubation buffer; a filtration is subsequently carried out. The filter-bound radioactivity is measured with a scintillation counter. Specific binding, that is, receptor-bound, is defined as the difference between total and unspecific-bound radioactivity. The unspecific binding is determined in the presence of an excess of non-radioactive nifedipine (1 $\mu$M).

The activity (potency) of a compound in this test is defined by the IC $_{50}$ and % maximum inhibition values (% max. inhibition). The IC $_{50}$ is the substance concentration (in mol/l) which produces a half-maximum inhibition of the specific $^3$H-nifedipine (or $^3$H-nitrendipine) binding. The maximum inhibition of the specific binding is given by the % maximum inhibition value; this value is established as 100% for the reference compound nifedipine. Both parameters are extrapolated from a concentration-binding curve.

B. Haemodynamic parameters in the narcotized dog
The 4 most important measurement parameters (with respective measurement units) of the haemodynamic experiment are: (1) CBF: Coronary Blood Flow (in ml/min)—the velocity of blood flow through the coronary arteries; (2) HR: heart rate (in beats/min)—the heart frequency; (3) Bp: blood pressure (in mm Hg)—the blood pressure; and (4) dp/dt: rate of increase in left ventricular pressure (in mm Hg/sec)—the rate of increase of the left ventricular pressure, as a measurement of the contractility force of the heart. The values are given as the % maximum variation from the initial value ($\Delta$%) and the duration of this variation (t) per dosage administered.

There is thus obtained not only an overall picture of the activity of the substance, but also an estimation as to the potential selectivity for a specific part of the circulatory system in the entire organism. After the administration of an anaesthetic, the dog is intubated and respired artificially. Blood pH, pCO$_2$, pO$_2$ and haemoglobin are measured hourly with a blood-gas analyzer. The blood pressure (systolic and diastolic) is measured with a probe in the aorta abdominalis. The heart frequency is recorded by means of a tachometer which is disengaged from the pressure pulse. For the other measurements the heart must firstly be opened in order that a probe can be inserted in the left ventricle (heart chamber) for the pressure measurements (dp/dt). The coronary blood flow is measured with a flowing probe in the left coronary artery (descendens).

The results obtained in these tests are compiled in the following Table:

TABLE

| Compound | A | | B | | | | Dosage mg/kg. p.o. |
|---|---|---|---|---|---|---|---|
| | IC$_{50}$ [M] | % max. inhib. | CBF ml/min. t | HR beats/min. t | Bp mm Hg t | dp/dt mm Hg/sec. t | |
| A | $4.4.10^{-9}$ | 100 | 50 (60°) | −19 (40°) | −55 (60°) | −42 (60°) | 0.03 |
| B | $9.5.10^{-9}$ | 100 | 78 (40°) | −11 (>30°) | −30 (24°) | −2 (20°) | 0.03 |
| C | $9.0.10^{-9}$ | 100 | 108 (20°) | −11 (>60°) | −32 (>60°) | −16 (>60°) | 0.03 |

A = 5-(Dimethylsulphamoyl)-1,4-dihydro-2,6-dimethyl-4-(3-nitrophenyl)nicotinic acid 2-propoxyethyl ester
B = 5-(Butylmethylsulphamoyl)-1,4-dihydro-2,6-dimethyl-4-(3-nitrophenyl)nicotinic acid isopropyl ester
C = 1,4-Dihydro-2,6-dimethyl-5-[(2-methoxyethyl)methysulphamoyl]-4-(3-nitrophenyl)nicotinic acid isopropyl ester The compounds of formula I can be used as medicaments for example, in the form of pharmaceutical preparations. The pharmaceutical preparations can be administered orally. for example, in the form of tablets, coated tablets, dragees, hard and soft gelatine capsules, solutions, emulsions or suspensions. The administration can however, also be carried out rectally for example. in the form of suppositories, or parenterally, for example, in the form of injection solutions.

For the preparation of tablets, coated tablets dragees and hard gelatine capsules the compounds of formula I can be processed with pharmaceutically inert inorganic or organic excipients. As such excipients there can be used for example for tablets, dragees and hard gelatine capsules, lactose maize starch or derivatives thereof, talc, stearic acid or its salts or the like.

For soft gelatine capsules, there are suitable as excipients, for example, vegetable oils waxes, fats semi-solid liquid polyols and the like.

For the preparation of solutions and syrups, suitable as excipients are for example, water, polyols, saccharose, invert sugar glucose and the like.

For injection solutions, suitable as excipients are. for example, water alcohols, polyols, glycerine vegetable oils and the like.

For suppositories, suitable as excipients are for example, natural or hardened oils, waxes, fats semi-liquid liquid polyols and the like.

Moreover, the pharmaceutical preparations can contain preservatives, solubilizers, stabilizing agents, wetting agents, emulsifying agents, sweetening agents, coloring agents, flavoring agents salts for varying the osmotic pressure, buffers, coating agents or antioxidants. They can also contain still other therapeutically valuable substances.

In accordance with the invention, compounds of formula I can be used in the control or prevention of angina pectoris, ischemia, high blood pressure and migraine. The dosage can vary within wide limits and will, of course, be adjusted to the individual reguirements in each particular case. In general, in the case of oral administration a daily dosage of about 10 to 100 mg of a compound of formula I should be appropriate whereby, however, the upper limit just given can also be exceeded when this is shown to be indicated.

The following Examples further illustrate the invention. All temperatures are given in degrees Celsius. unless otherwise stated.

Example 1

A solution of 3.0 g (0.001 mol) of α-acetyl-N,N-dimethyl-3-nitrostyrenesulfonamide and 1.43 g (0.01 mol) of 3-aminocrotonic acid isopropyl ester in 30 ml of isopropanol is heated to reflux for 2 hours thereupon treated with 1.16 q (0.005 mol) of DL-camphor-10-sulfonic acid and then heated to reflux for an additional 15 minutes. After concentration under reduced pressure, the oily residue is partitioned between water and methylene chloride the organic phase is washed with a saturated aqueous solution of sodium chloride, dried over sodium sulfate and concentrated graphed on 350 g of silica gel with methylene chloride/ethyl acetate (9:1) as the elution agent. The homogeneous fractions yield an oil which crystallizes upon trituration with ether. After recrystallization from methylene chloride/ether, there are obtained 3.2 g (75.5%) of 5-(di-methylsulfamoyl)-1.4-dihydro-2,6 -dimethyl-4-(3-nitrophenyl)-nicotinic acid isopropyl ester, m.p. 136°–138°, as a yelloWish crystalline powder.

The α-acetyl-N,N-dimethyl-3-nitrostyrenesulfonamide used as the starting material can be prepared as follows:

A solution of 20 g (0.16 mol) of N,N-dimethylmethanesulfonamide in 200 ml of dry tetrahydrofuran is treated dropwise under argon firstly at 15°–20° with 100 ml (0.16 mol) of a 1.6 molar n-butyl lithium solution in hexane and then at 10°–15° with a solution of 14.5 g (0.08 mol) ⓒf acetic acid 4-nitrophenyl ester in 40 ml of dry tetrahydrofuran. The temperature is then allowed to rise to room temperature (about 30 minutes) and the mixture is stirred for an additional 30 minutes. After concentration under reduced pressure the black residue is partitioned between 350 ml of ice-water and 150 ml of ether. The aqueous phase is acidified with 100 ml of 2N hydrochloric acid and extracted with methylene chloride. The extracts, dried over sodium sulfate, are then evaporated to dryness. The residual oil is chromatographed on 500 g of silica gel with toluene/ethyl acetate (4:1) as the elution agent. The uniform fractions yield 10.2 g (38%) of N,N-dimethyl-2-oxopropanesulfonamide as an oil which can be used for the next step without further purification. The oil crystallizes slowly upon standing. For the analysis, a sample is sublimed in a high vacuum. whereby colorless crystals. m.p. 47°–49° are obtained.

A solution of 4.1 g (0.025 mol) of N,N-dimethyl-2-oxopropanesulfonamide and 3.8 g (0.025 mol) of 3-nitrobenzaldehyde in 25 ml of benzene is treated with 0.1 ml of piperidine and 0.3 ml of glacial acetlc acid and the mixture is thereupon heated to reflux for 1 hour with the separation of water. The reaction solution is then concentrated to dryness under reduced pressure the residue is dissolved in 20 ml of toluene and the solution obtained is again evaporated to dryness. The residual oil is chromatographed on 170 g of silica gel with methylene chloride as the elution agent. The uniform fractions yield 4.3 g (58%) of α-acetyl-N,N-dimethyl-3-nitrostyrenesulfonamide m.p. 115°–120°, as a colorless crystalline powder.

EXAMPLE 2

The following compounds were obtained in an analogous manner to that described in Example 1:

5-(Dimethylsulfamoyl)-1.4-dihydro-2,6-dimethyl-4-(3-nitrophenyl)nicotinic acid methyl ester m.p. 166°–169°, from α-acetyl-N,N-dimethyl-3-nitrostyrenesulfonamide and 3-aminocrotonic acid methyl ester;

5-(dimethylsulfamoyl)-1 4-dihydro-2.6-dimethyl-4-(3-nitrophenyl)nicotinic acid 2-propoxyethyl ester, m.p. 74°–77°, from α-acetyl-N,N-dimethyl-3-nitrostyrenesulfonamide and 3-aminocrotonic acid 2-propoxyethyl ester;

5-(butylmethylsulfamoyl)-1.4-dihydro-2,6-dimethyl-4-(3-nitrophenyl)nicotinic acid isopropyl, ester. m.p. 80°–83°, from α-acetyl-N-butyl-N-methyl-3-nitrostyrenesulfonamide and 3-aminocrotonic acid isopropyl ester;

5-(diethylsulfamoyl)-1,4-dihydro-2 6-dimethyl-4-(3-nitrophenyl)nicotinic acid isopropyl ester, m p. 133°–136° , from α-acetyl-N,N-diethyl-3-nitrostyrenesulfonamide and 3-aminocrotonic acid isopropyl ester;

1,4-dihydro-2,6-dimethyl-4-(3-nitrophenyl)-5-(1-pyrrolidinylsulfonyl)nicotinic acid isopropyl ester m.p. 169°–172° , from 4-(3-nitrophenyl)-3-(1-pyrrolidinylsulfonyl)-3-buten-2-one and 3-aminocrotonic acid isopropyl ester, and 1,4-dihydro-2,6-dimethyl-5-[(2-methoxyethyl)methylsulfamoyl]-4-(3-nitrophenyl)nicotinic acid isopropyl ester, m.p. 86°–88°, from α-acetyl-N-(2-methoxyethyl)-N-methyl- -3-nitrostyrenesulfonamide and 3-aminocrotonic acid isopropyl ester.

The following 3-nitrostyrenesulfonamides used as starting materials were also prepared in an analogous manner to that described in Example 1:

α-Acetyl-N-butyl-N-methyl-3-nitrostyrenesulfonamide in the form of a thick oil;

α-acetyl-N,N-diethyl-3-nitrostyrenesulfonamide. m.p. 112°–115°:

4-(3-nitrophenyl)-3-(1-pyrrol ldinylsulfonyl)-3-buten-2-one. m.p. 123°–126°, and α-acetyl-N-(2-methoxyethyl)-N-methyl-3-nitrostyrenesulfonamide m.p. 86°–88°.

EXAMPLE 3

A solution of 3.12 g (0.01 mol) of α-acetyl-N-isopropyl-3-nitrostyrenesulfonamide in 30 ml of isopropanol is treated with 1.87 g (0.01 mol) of 3-aminocrotonic acid 2-propoxyethyl ester and 1.16 g (0.005 mol) of DL-camphor-10-sulfonic acid in accordance with the procedure described in Example 1. After chromatography on silica gel with methylene chloride/ethyl acetate (4:1) as the elution agent the crude product is recrystallized from isopropanol. There is obtained 1.0 g (21%) of 5-(isopropylsulfamoyl)-1,4-dihydro-2.6-dimethyl-4-(3 -nitrophenyl)nicotinic acid 2-propoxyethyl ester, m.p. 155°-158°, as a colorless crystalline powder.

The α-acetyl-N-isopropyl-3-nitrostyrenesulfonamide used as the starting material can be prepared as follows:

A solution of 16.8 g (0.16 mol) of N-isopropylmethanesulfonamide in 200 ml of dry tetrahydrofuran is treated with 200 ml (0.32 mol) of a 1.6 molar n-butyl lithium solution in hexane and 14.5 g (0.08 mol) of acetic acid 4-nitrophenyl ester in 40 ml of dry tetrahydrofuran in accordance with the procedure described in Example 1. The crude product is chromatographed on 1000 g of silica gel with methylene chloride/ethyl acetate (9:1) as the elution agent. The homogeneous fractions yield 7.5 g of N-isopropyl-2-oxopropanesulfonamide as an oil which can be used for the next step without further purification.

A solution of 7.5 g (about 0.04 mol) of N-isopropyl-2--oxopropanesulfonamide and 6.0 g (0.04 mol) of 3-nitrobenzaldehyde in 40 ml of benzene is treated with 0.16 ml of piperidine and 0.48 ml of glacial acetic acid in an analogous manner to that described in Example 1. The oily crude product is triturated with ether, whereby crystallization occurs. There are obtained 2.5 g of α-acetyl-N- -isopropyl-3-nitrostyrenesulfonamide in the form of colorless crystals, m.p. 153°-157°.

EXAMPLE 4

A solution of 3.67 g (0.01 mol) of α-(cyclohexylcarbonyl)-N,N-dimethyl-3 -nitrostyrenesulfonamide in 30 ml of isopropanol is treated with 1.15 g (0.01 mol) of 3-aminocrotonic acid methyl ester and 1.16 g (0.005 mol) of DL-camphor-10-sulfonic acid in accordance with the procedure described in Example 1. After chromatography on silica gel with methylene chloride/ethyl acetate (9:1) as the elution agent the crude product is recrystallized from acetonitrile. There are obtained 1.5 g (32%) of 6-cyclohexyl-5-(dimethylsulfamoyl)-1,4 -dihydro-2-methyl-4-(3-nitrophenyl)nicotinic acid methyl ester, m.p 185°-188°, as a colorless crystalline powder.

The α-(cyclohexylcarbonyl)-N,N -dimethyl-3-nitrostyrenesulfonamide used as the starting material is prepared from 5.8 g (0.025 mol) of 2-cyclohexyl-N,N-dimethyl-2-oxoethanesulfonamide and 3.8 g (0.025 mol) of 3-nitrobenzaldehyde in an analogous manner to that described in Example 1. After chromatography on silica gel with methylene chloride as the elution agent, there are obtained 5.9 g (66%) of α-(cyclohexylcarbonyl)-N,N-dimethyl-3-nitrostyrenesulfonamide in the form of colorless crystals, m.p. 115°-118°.

EXAMPLE 5

A solution of 4.27 g (0.01 mol) of 6-(α-acetyl-N-methyl-3-nitrostyrenesulfonamido)caproic acid ethyl ester in 30 ml of ethanol is treated with 1.15 g (0.01 mol) of 3-aminocrotonic acid methyl ester and 1.16 g (0.005 mol) of DL-camphor-10-sulfonic acid analogously to Example 1. After chromatography on silica gel with methylene chloride/ethyl acetate (9:1) as the elution agent the crude product is recrystallized from methylene chloride/ether There are obtained 3.4 g (65%) of 5-{[5-(ethoxycarbonyl)pentyl]methylsulfamoyl}-1,4 -dihydro-2,6-dimethyl-4-(3-nitrophenyl)nicotinic acid methyl ester,. m.p. 83°-86°, as a colorless crystalline powder.

The 6-(α-acetyl-N-methyl-3 -nitrostyrenesulfonamido)caproic acid ethyl ester used as the starting material can be prepared as follows:

A solution of 72.7 g (0.4 mol) of 6-aminocaproic acid methyl ester hydrochloride in 2000 ml of methylene chloride is treated at 20°-25° firstly with 140 ml (1.0 mol) of triethylamine and then with a solution of 38 ml (0.48 mol) of methanesulfochloride in 160 ml of methylene chloride. The mixture is subsequently stirred at room temperature for 90 minutes and thereupon treated with 800 ml of 0.5N hydrochloric acid. The organic phase is washed with saturated aqueous solutions of sodium bicarbonate and sodium chloride and dried over sodium sulfate. After concentration under reduced pressure the residual oil is dissolved in 400ml of dimethylformamide, treated at 15°-20° with a solution of 0.48 mol of sodium methylate (from 11.0 g of sodium) in 100 ml of methanol and thereupon stirred at room temperature for 30 minutes. The methanol is then distilled off at 50° under reduced pressure and the residual solution is treated at 15°-20° with a solution of 48 ml (0.8 mol) of methyl iodide in 100 ml of dimethylformamide. The reaction mixture is then stirred at room temperature for an additional 15 minutes and thereupon concentrated to dryness under reduced pressure. The residue is partitioned between water and methylene chloride and the organic phase is washed with a saturated aqueous sodium chloride solution dried over sodium sulfate and evaporated to dryness. There are obtained 90 g (95%) of 6-[(methylsulfonyl)methylamino]caproic acid methyl ester as an oil which can be used for the next step without further purification.

A mixture of 90 g (0.38 mol) of 6-[(methylsulfonyl)methylamino]caproic acid methyl ester and 67.5 g (0.76 mol) of 2-amino-2-methyl-1-propanol is stirred at 135° for 16 hours. The reaction mixture is partitioned between 500 ml of methylene chloride and 250 ml of 2N hydrochloric acid and the organic phase is washed with a saturated aqueous sodium chloride solution, dried over sodium sulfate and concentrated to dryness. The residual oil crystallizes upon trituration with ether. There are obtained 85.2 g (76%) of N-(2 -hydroxy-1,1-dimethylethyl)-6-[(methylsulfonyl)methylamino]capronamide, m.p. 77°-80°, as a colorless crystal powder. For analysis, a sample is recrystallized from ethyl acetate m.p. 84°-87°.

A solution of 82.5 g (0.28 mol) of N-(2-hydroxy-1,1-dimethylethyl)-6-[(methylsulfonyl)methylamino]capronamide in 525 ml of methylene chloride is treated at a temperature between −5 and 0° with a solution of 46.5 ml (0.64 mol) of thionyl chloride in 175 ml of methylene chloride. Thereupon, the temperature is allowed to rise to 20° within 15 minutes. The solution is stirred at room temperature for an additional 45 minutes and thereafter again cooled to 0° . The reaction mixture is then treated at 0°-5° with a solution of 220 g of potassium carbonate in 880 ml of water and thereupon stirred for an additional 15 minutes without cooling. The organic phase is then washed with a saturated aqueous sodium chloride solution, dried over sodium sulfate and concentrated to dryness. The residual oil is chromatographed on 1000 g of silica gel with ethyl acetate/ethanol (9:1) as the elution agent. The homogeneous fractions yield 62.2 g (80%) of 4,5-dihydro-4,4-dimethyl-2-{5-[(methylsulfonyl)methylamino]pentyl}-oxazole as a yellow oil.

A solution of 22.1 g (0.08 mol) of 4,5-dihydro-4,4-dimethyl-2 -{5-[(methylsulfonyl)methylamino]pentyl}oxazole in 100 ml of dry tetrahydrofuran is treated with 0.08 mol of butyl lithium and 7.25 g (0.04 mol) of acetic acid 4-nitrophenyl ester in accordance with the procedure described in Example 1. After concentration under reduced pressure, the residue is partitioned between water and ether, the aqueous phase is acidified with 80 ml of 2N hydrochloric acid and extracted with methylene chloride. The aqueous solution is then adjusted to pH 7 with 2N sodium hydroxide solution and again extracted with methylene chloride. The extracts, dried over sodium sulfate, are then evaporated to dryness. The residue is chromatographed on 250 g of silica gel with ethyl acetate/ethanol (9:1) as the elution agent. There are obtained 7 g of 4,5-dihydro-4,4-dimethyl-2-}5-[(2-oxopropylsulfonyl)-methylamino]pentyl}oxazole as an oil which still contains about 30% of the starting oxazole in accordance with NMR data.

This oil (7.0 g) is dissolved in a mixture of 70 ml of ethanol and 2.5 ml of sulfuric acid and the resulting solution is heated to reflux for 12 hours. The reaction mixture is then poured on to 140 ml of ice-water and extracted with methylene chloride. The organic extracts are combined, washed with saturated aqueous sodium chloride solution and dried over sodium sulfate. After concentration under reduced pressure, the oily residue is chromatographed on 150 g of silica gel with ethyl acetate/ethanol (9:1) as the elution agent. There are obtained 6.5 g of 6-[(2-oxopropylsulfonyl)methylamino]caproic acid ethyl ester as an oil which contains about 30% of 6-[(methylsulfonyl)methylamino]caproic acid ethyl ester in accordance with NMR data.

This mixture (6.5 g) is treated with 3.0 g (0.02 mol) of 3-nitrobenzaldehyde, 0.08 ml of piperidine and 0.24 ml of glacial acetic acid in 20 ml of benzene in an analogous manner to that described in Example 1. The oily crude product is chromatographed on 250 g of silica gel firstly with methylene chloride and then with methylene chloride/ethyl acetate (9:1) as the elution agent. The uniform fractions yield an oil which crystallizes upon trituration with ether. There are obtained 5.35 g of 6-(α-acetyl-N-methyl-3-nitrostyrenesulfonamido)caproic acid ethyl ester in form of colorless crystals. m.p. 60°–63°.

EXAMPLE 6

A solution of 3.42 g (0.01 mol) of α-acetyl-N-(2- -methoxyethyl)-N-methyl-3-nitrostyrenesulfonamide and 1.87 g (0.01 mol) of 3-aminocrotonic acid 2-propoxyethyl ester in 15 ml of isopropanol is heated to reflux for 2 hours, thereupon treated with 1.0 g of Amberlyst ® 15 as the catalyst and then heated to reflux for an additional 30 minutes. After concentration under reduced pressure 0 the oily residue is dissolved in methylene chloride, the catalyst remaining behind is removed by filtration under suction, and the filtrate is washed with a saturated aqueous sodium chloride solution, dried over sodium sulfate and concentrated to dryness. The residual oil is chromatographed on 300 g of silica gel with methylene chloride/ethyl acetate (4:1) as the elution agent. The uniform fractions yield an oil which crystallizes upon trituration and leaving to stand under hexane. After recrystallization from ether, there are obtained 2.4 g (47%) of 1,4-dihydro-2 6-dimethyl-5-[(2-methoxyethyl)methylsulfamoyl]-4-(3-nitrophenyl)nicotinic acid 2-propoxyethyl ester. m.p. 67°–70°, as an almost colorless crystalline powder.

EXAMPLE 7

The following compounds were prepared in an analogous manner to that described in Example 6:

4-(3-Chlorophenyl)-1,4-dihydro-2 6 -dimethyl-5-[(2-methoxyethyl)methylsulfamoyl]nicotinic acid isopropyl ester, m.p. 76°–79°, from α-acetyl-3-chloro-N-(2-methoxyethyl)-N-methylstyrenesulfonamide and 3-aminocrotonic acid isopropyl ester;

4-(3-chlorophenyl)-1 4-dihydro-2 6-dimethyl-5-[(2-methoxyethyl)methylsulfamoyl]nicotinic acid 2-propoxyethyl ester, m.p. 83°–85°, from α-acetyl-3-chloro-N-(2-methoxyethyl)-N-methylstyrenesulfonamide and 3-aminocrotonic acid 2-propoxyethyl ester;

4-(2.3-dichlorophenyl)-1 4-dihydro-2.6-dimethyl-5-[(2-methoxyethyl)methylsulfamoyl]nicotinic acid isopropyl ester, m.p. 134°–136°, from α-acetyl-2.3-dichloro-N(2-methoxyethyl)-N-methylstyrenesulfonamide and 3-aminocrotonic acid isopropyl ester;

1,4-dihydro-5-dimethylsulfamoyl-2,6-dimethyl-4-(2-trifluoromethylphenyl)nicotinic acid methyl ester, m.p. 205°–208°, from α-acetyl-N,N-dimethyl-2-trifluoromethyl-styrenesulfonamide and 3-aminocrotonic acid methyl ester;

4-(2-chlorophenyl)-1 4-dihydro-2 6 -dimethyl-5-[(2 -methoxyethyl)methylsulfamoyl]nicotinic acid isopropyl ester, m.p. from α-acetyl-2-chloro-N-(2-methoxyethyl)-N-methylstyrenesulfonamide and 3-aminocrotonic acid isopropyl ester;

5-(butylmethylsulfamoyl)-4-(2-chlorophenyl)-1,4-dihydro-2.6-dimethylnicotinic acid isopropyl ester, m.p 98°–101°, from α-acetyl-2-chloro-N-butyl-N-methylstyrenesulfonamide and 3-aminocrotonic acid isopropyl ester;

5-(butylmethylsulfamoyl)-1.4-dihydro-2,6-dimethyl-4-(3-nitrophenyl)nicotinic acid cyclopropylmethyl ester. m.p. 93°–96°, from α-acetyl-N-butyl-N-methyl-3-nitrostyrenesulfonamide and 3-aminocrotonic acid cyclopropylmethyl ester and 5-(butylmethylsulfamoyl)-1,4-dihydro-2,6-dimethyl-4-(2-pyridyl)nicotinic acid isopropyl ester, m.p. 119°–122°, from N-butyl-N-methyl-2-oxo-1-(2-pyridylmethylene)propanesulfonamide and 3-aminocrotonic acid isopropyl ester.

The following styrenesulfonamides used as starting materials were prepared in a manner analogous to that described in Example 1:

α-Acetyl-3-chloro-N-(2-methoxyethyl)-N-methyl-styrenesulfonamide in the form of a thick oil;

α-acetyl-2,3-dichloro-N-(2-methoxyethyl)-N-methyl-styrenesulfcnamide m.p. 55°–58°;

α-acetyl-N,N-dimethyl-2-trifluoromethylstyrenesulfonamide in the form of a thick oil;

α-acetyl-2-chloro-N-(2-methoxyethyl)-N-methyl-styrenesulfonamide m.p. 76°–79°;

α-acetyl-2-chloro-N-butyl-N-methylstyrenesulfonamide, m.p. 65°–67°, and

N-butyl-N-methyl-2-oxo-1-(2-pyridylmethylene)-propanesulfonamide, m.p. 59°–61°.

EXAMPLE A

Preparation of tablets of the following composition:

| | | |
|---|---|---|
| I. | 5-(Butylmethylsulfamoyl)-1,4-dihydro-2,6-dimethyl-4-(3-nitrophenyl)nicotinic acid isopropyl ester, micronized | 20.0 mg |
| | Lactose powder | 40.0 mg |
| | Maize starch white | 24.9 mg |

-continued

| | | |
|---|---|---|
| II. | Dioctyl sodium sulfosuccinate | 0.1 mg |
| | Maize starch white | 5.0 mg |
| | Water | q.s |
| III. | Maize starch white | 6.0 mg |
| IV. | Talc | 3.0 mg |
| | Magnesium stearate | 1.0 mg |
| | | 100.0 mg |

The substances of phase I are sieved and mixed. This mixture is moistened with the maize starch paste II and kneaded. The moist mass is granulated, dried and converted into a suitable particle size. Phase III is admixed. This mixture is mixed with phase IV for a short time.

The ready-to-press mixture is pressed into tablets of mg with a break-bar.

EXAMPLE B

Preparation of tablets of the following composition:

| | | |
|---|---|---|
| I. | 5-(Butylmethylsulfamoyl)-1,4-dihydro-2,6-dimethyl-4-(3-nitrophenyl)nicotinic acid isopropyl ester | 200.0 mg |
| | Lactose Powder | 42.9 mg |
| | Maize starch white | 50.0 mg |
| II. | Dioctyl sodium sulfosuccinate | 0.1 mg |
| | Maize starch white | 20.0 mg |
| | Water | q.s |
| III. | Maize starch white | 30.0 mg |
| IV. | Talc | 3.5 mg |
| | Magnesium stearate | 3.5 mg |
| | | 350.0 mg |

The substances of phase I are sieved and mixed. This mixture is moistened with the maize starch paste II and kneaded. The moist mass is granulated dried and converted into a suitable particle size. Phase III is admixed. This mixture is mixed with phase IV for a short time. The ready-to-press mass is pressed into tablets of mg with a break-bar.

EXAMPLE C

Preparation of capsules of the following composition:

| | | |
|---|---|---|
| I. | 5-(Butylmethylsulfamoyl)1,4-dihydro-2,6-dimethyl-4-(3-nitrophenyl)nicotinic acid isopropyl ester, micronized | 20.0 mg |
| | Lactose powder | 48.0 mg |
| II. | Maize starch | 5.0 mg |
| | Water | q.s |
| III. | Lactose crystalline | 50.0 mg |
| | Maize starch | 15.0 mg |
| IV. | Talc | 10.0 mg |
| | Magnesium stearate | 2.0 mg |
| | | 150.0 mg |

The substances of phase 1 are sieved and miXed. This mixture is moistened with the maize starch paste II and kneaded. The moist mass is granulated dried and converted into a suitable particle size. Phase III is admixed. This mixture is mixed with phase IV for a short time.

The capsule mixture is filled into size 2 capsules each containing 150 mg.

EXAMPLE D

An aqueous drop suspension of the following composition is prepared;

| | |
|---|---|
| 5-(Butylmethylsulfamoyl)-1,4-dihydro-2,6-dimethyl-4-(3-nitrophenyl)nicotinic acid isopropyl ester | 0.05 g |
| Sodium benzoate | 0.035 g |
| Saccharin sodium | 0.015 g |
| Acrylic acid polymerizate | 0.1–1.0 g |
| Saccharose | 3.5 g |
| Citric acid | 0.025 g |
| Polyoxyethylene stearate | 0.002–0.01 g |
| Sodium hydroxide | q.s |
| Flavor | q.s |
| Food coloring | q.s |
| Water deionized | ad 10.0 ml |

EXAMPLE E

When the procedures described in Examples A-D are followed, tablets, capsules and injection preparations can be prepared from the following, likewise preferred compounds:

5-(Dimethylsulfamoyl)-1,4-dihydro-2 6-dimethyl-4-(3-nitrophenyl)nicotinic acid 2-propoxyethyl ester and 1,4-dihydro-2 6-dimethyl-5-[(2-methoxyethyl)methylsulfamoyl]-4-(3-nitrophenyl)nicotinic acid isopropyl ester.

We claim:

1. A compound of the formula

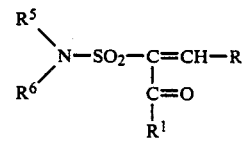

II wherein R is naphthyl or phenyl optionally monosubstituted by $c_1$–$C_6$-alkyl, halogen, trifluoromethyl or nitro or optionally disubstituted by halogen or halogen and nitro; imidazolyl; or pyridyl, $R^1$ is $C_1$–$C_4$-alkyl or $C_3$–$C_6$-cycloalkyl, $R^5$ is hydrogen, $C_1$–$C_6$-alkyl or $C_3$–$C_6$-cycloalkyl, $R^6$ is $C_1$–$C_6$-alkyl, $C_3$–$C_6$-cycloalkyl, $C_3$–$C_6$-cycloalkyl-$C_1$–$C_6$-alkyl, $C_1$–$C_6$-alkoxy-$C_1$–$C_6$alkyl, $C_1$–$C_6$-alkoxy-$C_1$–$C_6$-alkoxy-$C_1$–$C_6$-alkyl, Chd 1-$C_6$-alkylthio-$C_1$–$C_6$-alkyl, $C_1$–$C_6$-alkoxycarbonyl-$C_2$–$C_6$-alkyl or $R^5$ and $R^6$ taken together are the group —$CH_2CH_2$—O-$CH_2CH_2$—or a —$(CH_2)_n$—group in which n is an integer of 2 to 7.

2. A compound in accordance with claim 1, α-acetyl-N, N-dimethyl-3-nitrostyrenesulfonamide.

3. A compound in accordance with claim 1, α-acetyl-n-butyl-N-methyl-3-nitrostyrenesulfonamide.

4. A compound in accordance with claim 1, α-acetyl-N, N-diethyl-3-nitrostyrenesulfonamide.

5. A compound in accordance with claim 1, α-acetyl-N-(2-methoxyethyl)-N-methyl-3-nitrostyrenesulfonamide.

6. A compound in accordance with claim 1, α-(cyclohexylcarbonyl)N,N -dimethyl-3-nitrostyrenesulfonamide.

* * * * *

UNITED STATES PATENT AND TRADEMARK OFFICE
CERTIFICATE OF CORRECTION

PATENT NO. : 4,994,612

DATED : February 19, 1991

INVENTOR(S) : ROLAND JUANIN and HENRI RAMUZ

It is certified that error appears in the above-identified patent and that said Letters Patent is hereby corrected as shown below:

Claim 1, Column 14, Line 40 delete "$c_1$" and insert --- $C_1$ ---.

Claim 1, Column 14, Line 45 delete "$C_1-C_6 alkyl$" and insert --- $C_1-C_6$-alkyl ---.

Claim 1, Column 14, Line 46 delete "$Chdl-C_6$" and insert --- $C_1-C_6$ ---.

Signed and Sealed this

Fifteenth Day of September, 1992

*Attest:*

DOUGLAS B. COMER

*Attesting Officer*   *Acting Commissioner of Patents and Trademarks*